(12) United States Patent
Gyrn

(10) Patent No.: US 8,790,311 B2
(45) Date of Patent: Jul. 29, 2014

(54) MOUNTING PAD

(75) Inventor: Steffen Gyrn, Ringsted (DK)

(73) Assignee: Unomedical A/S, Bireröd (DK)

( * ) Notice: Subject to any disclaimer, the term of this patent is extended or adjusted under 35 U.S.C. 154(b) by 1503 days.

(21) Appl. No.: 12/303,676

(22) PCT Filed: Jun. 8, 2007

(86) PCT No.: PCT/DK2007/000278
§ 371 (c)(1),
(2), (4) Date: Mar. 7, 2011

(87) PCT Pub. No.: WO2007/140785
PCT Pub. Date: Dec. 13, 2007

(65) Prior Publication Data
US 2011/0152778 A1 Jun. 23, 2011

Related U.S. Application Data

(60) Provisional application No. 60/812,469, filed on Jun. 9, 2006, provisional application No. 60/876,689, filed on Dec. 22, 2006.

(30) Foreign Application Priority Data

Jun. 9, 2006 (DK) .................................. 2006 00779

(51) Int. Cl.
*A61M 25/02* (2006.01)
(52) U.S. Cl.
USPC ........................................................ 604/180

(58) Field of Classification Search
USPC ......... 604/180, 174; 206/441; 602/57, 52, 54; 53/429
See application file for complete search history.

(56) References Cited

U.S. PATENT DOCUMENTS

| 1,592,462 A | 7/1926 | MacGregor |
| 2,047,010 A | 7/1936 | Dickinson |
| 2,295,849 A | 9/1942 | Kayden |
| 2,690,529 A | 9/1954 | Lindblad |
| 2,972,779 A | 2/1961 | Cowley |
| 3,059,802 A | 10/1962 | Mitchell |
| 3,074,541 A | 1/1963 | Roehr |
| 3,149,186 A | 9/1964 | Coanda |

(Continued)

FOREIGN PATENT DOCUMENTS

| DE | 4 342 329 A1 | 6/1994 |
| DE | 196 31 921 A1 | 3/1997 |

(Continued)

*Primary Examiner* — Emily Schmidt
*Assistant Examiner* — Michael J Anderson
(74) *Attorney, Agent, or Firm* — Wilson, Sonsini, Goodrich & Rosati

(57) ABSTRACT

A mounting pad comprising an adhesive layer (2), said adhesive layer being provided with a removable release liner (3). The release liner being divided into at least two sections (3A, 3B) and each of the at least two said sections of the release liner is provided with one or more score lines (4) thereby defining each section of the release liner as a strip, which renders it possible by a single straight upward pull to peel a release liner in two or more narrow strips, thereby still maintaining an even pull with small force needed to remove the release liner and using only a short pulling distance for removing the release liner from the adhesive surface.

28 Claims, 8 Drawing Sheets

(56) References Cited

U.S. PATENT DOCUMENTS

| | | | |
|---|---|---|---|
| 3,221,739 A | 12/1965 | Rosenthal | |
| 3,221,740 A | 12/1965 | Rosenthal | |
| 3,306,291 A | 2/1967 | Burke | |
| 3,485,352 A | 12/1969 | Pilger | |
| 3,509,879 A | 5/1970 | Bathish et al. | |
| 3,519,158 A | 7/1970 | Anderson | |
| 3,547,119 A | 12/1970 | Hall et al. | |
| 3,575,337 A | 4/1971 | Bernhardt | |
| 3,610,240 A | 10/1971 | Harautuneian | |
| 3,615,039 A | 10/1971 | Ward | |
| 3,670,727 A | 6/1972 | Reiterman | |
| 3,783,895 A | 1/1974 | Weichselbaum | |
| 3,788,374 A | 1/1974 | Saijo | |
| 3,810,469 A | 5/1974 | Hurschman | |
| 3,835,862 A | 9/1974 | Villari | |
| 3,840,011 A | 10/1974 | Wright | |
| 3,893,448 A | 7/1975 | Brantigan | |
| 3,937,219 A | 2/1976 | Karakashian | |
| 3,986,507 A | 10/1976 | Watt | |
| 3,986,508 A | 10/1976 | Barrington | |
| 3,995,518 A | 12/1976 | Spiroff | |
| 4,022,205 A | 5/1977 | Tenczar | |
| 4,188,950 A | 2/1980 | Wardlaw | |
| 4,201,406 A | 5/1980 | Dennehey et al. | |
| 4,227,528 A | 10/1980 | Wardlaw | |
| 4,259,276 A | 3/1981 | Rawlings | |
| 4,267,836 A | 5/1981 | Whitney et al. | |
| 4,296,786 A | 10/1981 | Brignola | |
| 4,315,505 A | 2/1982 | Crandall et al. | |
| 4,333,455 A | 6/1982 | Bodicky | |
| 4,334,551 A | 6/1982 | Pfister | |
| D267,199 S | 12/1982 | Koenig | |
| 4,378,015 A | 3/1983 | Wardlaw | |
| 4,402,407 A | 9/1983 | Maly | |
| 4,415,393 A | 11/1983 | Grimes | |
| 4,417,886 A | 11/1983 | Frankhouser et al. | |
| 4,464,178 A | 8/1984 | Dalton | |
| 4,473,369 A | 9/1984 | Lueders et al. | |
| 4,484,910 A | 11/1984 | Sarnoff et al. | |
| 4,500,312 A | 2/1985 | McFarlane | |
| 4,508,367 A | 4/1985 | Oreopoulos et al. | |
| 4,525,157 A | 6/1985 | Vaillancourt | |
| 4,530,695 A | 7/1985 | Phillips et al. | |
| 4,531,937 A | 7/1985 | Yates | |
| 4,543,088 A | 9/1985 | Bootman et al. | |
| 4,563,177 A | 1/1986 | Kamen | |
| 4,610,469 A | 9/1986 | Wolff-Mooij | |
| 4,617,019 A | 10/1986 | Fecht | |
| 4,713,059 A | 12/1987 | Bickelhaupt et al. | |
| 4,734,092 A | 3/1988 | Millerd | |
| 4,755,173 A * | 7/1988 | Konopka et al. | 604/167.02 |
| 4,817,603 A | 4/1989 | Turner et al. | |
| RE32,922 E | 5/1989 | Levin et al. | |
| 4,838,871 A | 6/1989 | Luther | |
| 4,840,613 A | 6/1989 | Balbierz | |
| 4,850,974 A | 7/1989 | Bickelhaupt et al. | |
| 4,850,996 A | 7/1989 | Cree | |
| 4,863,016 A | 9/1989 | Fong et al. | |
| 4,878,897 A | 11/1989 | Katzin | |
| 4,890,608 A | 1/1990 | Steer | |
| 4,894,054 A | 1/1990 | Miskinyar | |
| 4,895,570 A | 1/1990 | Larkin | |
| 4,917,669 A | 4/1990 | Bonaldo | |
| 4,935,010 A | 6/1990 | Cox et al. | |
| 4,950,163 A | 8/1990 | Zimble | |
| 4,950,252 A | 8/1990 | Luther et al. | |
| 4,956,989 A | 9/1990 | Nakajima | |
| 4,970,954 A | 11/1990 | Weir et al. | |
| 4,978,338 A | 12/1990 | Melsky et al. | |
| 4,982,842 A | 1/1991 | Hollister | |
| 4,986,817 A | 1/1991 | Code | |
| 4,994,042 A | 2/1991 | Vadher | |
| 4,994,045 A | 2/1991 | Ranford | |
| 5,011,475 A | 4/1991 | Olsen | |
| 5,020,665 A | 6/1991 | Bruno | |
| 5,024,662 A | 6/1991 | Menes et al. | |
| 5,052,381 A * | 10/1991 | Gilbert et al. | 602/52 |
| 5,067,496 A | 11/1991 | Eisele | |
| 5,092,853 A | 3/1992 | Couvertier, II | |
| 5,098,389 A | 3/1992 | Cappucci | |
| 5,112,313 A | 5/1992 | Sallee | |
| 5,116,319 A | 5/1992 | Van den Haak | |
| 5,116,325 A | 5/1992 | Paterson | |
| 5,121,751 A | 6/1992 | Panalletta | |
| 5,129,884 A | 7/1992 | Dysarz | |
| 5,135,502 A | 8/1992 | Koenig, Jr. et al. | |
| 5,137,516 A | 8/1992 | Rand et al. | |
| 5,137,524 A | 8/1992 | Lynn et al. | |
| 5,141,496 A | 8/1992 | Dalto et al. | |
| 5,147,375 A | 9/1992 | Sullivan et al. | |
| 5,160,315 A * | 11/1992 | Heinecke et al. | 602/57 |
| 5,163,915 A | 11/1992 | Holleron | |
| 5,172,808 A | 12/1992 | Bruno | |
| 5,176,643 A | 1/1993 | Kramer et al. | |
| 5,176,650 A | 1/1993 | Haining | |
| 5,176,662 A | 1/1993 | Bartholomew et al. | |
| 5,186,712 A | 2/1993 | Kelso et al. | |
| 5,188,611 A | 2/1993 | Orgain | |
| RE34,223 E | 4/1993 | Bonaldo | |
| 5,205,820 A | 4/1993 | Kriesel | |
| 5,222,947 A | 6/1993 | D'Amico | |
| 5,232,454 A | 8/1993 | Hollister | |
| 5,248,301 A | 9/1993 | Koenig et al. | |
| 5,256,149 A | 10/1993 | Banik et al. | |
| 5,256,152 A | 10/1993 | Marks | |
| 5,257,980 A | 11/1993 | Van Antwerp et al. | |
| 5,267,963 A | 12/1993 | Bachynsky | |
| 5,269,799 A | 12/1993 | Daniel | |
| 5,271,744 A | 12/1993 | Kramer et al. | |
| 5,279,579 A | 1/1994 | D'Amico | |
| 5,279,591 A | 1/1994 | Simon | |
| 5,282,793 A | 2/1994 | Larson | |
| 5,300,030 A | 4/1994 | Crossman et al. | |
| 5,312,359 A | 5/1994 | Wallace | |
| 5,312,369 A | 5/1994 | Arcusin et al. | |
| 5,316,246 A | 5/1994 | Scott et al. | |
| 5,324,302 A | 6/1994 | Crouse | |
| 5,342,319 A | 8/1994 | Watson et al. | |
| 5,342,324 A | 8/1994 | Tucker | |
| 5,344,007 A | 9/1994 | Nakamura et al. | |
| 5,350,392 A | 9/1994 | Purcell et al. | |
| 5,354,280 A | 10/1994 | Haber et al. | |
| 5,354,337 A | 10/1994 | Hoy | |
| 5,366,469 A | 11/1994 | Steg et al. | |
| 5,372,592 A | 12/1994 | Gambale | |
| 5,372,787 A | 12/1994 | Ritter | |
| 5,376,082 A | 12/1994 | Phelps | |
| 5,379,895 A | 1/1995 | Foslien | |
| 5,384,174 A * | 1/1995 | Ward et al. | 428/41.5 |
| 5,387,197 A | 2/1995 | Smith et al. | |
| 5,390,669 A | 2/1995 | Stuart et al. | |
| 5,391,151 A | 2/1995 | Wilmot | |
| 5,397,297 A * | 3/1995 | Hunter | 602/54 |
| 5,403,288 A | 4/1995 | Stanners | |
| 5,405,332 A | 4/1995 | Opalek | |
| 5,425,715 A | 6/1995 | Dalling et al. | |
| 5,429,607 A | 7/1995 | McPhee | |
| 5,429,613 A | 7/1995 | D'Amico | |
| 5,439,473 A | 8/1995 | Jorgensen | |
| D362,718 S | 9/1995 | Deily et al. | |
| 5,449,349 A | 9/1995 | Sallee et al. | |
| 5,451,210 A | 9/1995 | Kramer et al. | |
| 5,478,316 A | 12/1995 | Bitdinger et al. | |
| 5,490,841 A | 2/1996 | Landis | |
| 5,501,675 A | 3/1996 | Erskine | |
| 5,505,709 A | 4/1996 | Funderburk et al. | |
| 5,507,730 A | 4/1996 | Haber et al. | |
| 5,514,117 A | 5/1996 | Lynn | |
| 5,520,629 A * | 5/1996 | Heinecke et al. | 602/57 |
| 5,520,654 A | 5/1996 | Wahlberg | |
| 5,522,803 A | 6/1996 | Teissen-Simony | |
| 5,527,287 A | 6/1996 | Miskinyar et al. | |
| 5,533,974 A | 7/1996 | Gaba | |
| 5,540,709 A | 7/1996 | Ramel | |

(56) References Cited

U.S. PATENT DOCUMENTS

| | | | |
|---|---|---|---|
| 5,545,143 A * | 8/1996 | Fischell ............. 604/180 |
| 5,545,152 A | 8/1996 | Funderburk et al. |
| 5,549,577 A | 8/1996 | Siegel et al. |
| 5,554,130 A | 9/1996 | McDonald et al. |
| 5,558,650 A | 9/1996 | McPhee |
| 5,562,629 A | 10/1996 | Haughton et al. |
| 5,562,636 A | 10/1996 | Utterberg |
| 5,573,510 A | 11/1996 | Isaacson |
| 5,575,777 A | 11/1996 | Cover et al. |
| 5,584,813 A | 12/1996 | Livingston et al. |
| 5,586,553 A | 12/1996 | Halili |
| 5,591,188 A | 1/1997 | Waisman |
| 5,599,309 A | 2/1997 | Marshall et al. |
| 5,599,315 A | 2/1997 | McPhee |
| 5,599,318 A | 2/1997 | Sweeney et al. |
| 5,628,765 A | 5/1997 | Morita |
| 5,643,214 A | 7/1997 | Marshall |
| 5,643,216 A | 7/1997 | White |
| 5,643,220 A | 7/1997 | Cosme |
| 5,658,256 A | 8/1997 | Shields |
| 5,662,617 A | 9/1997 | Odell et al. |
| 5,665,071 A | 9/1997 | Wyrick |
| 5,665,075 A | 9/1997 | Gyure et al. |
| 5,676,156 A | 10/1997 | Yoon |
| 5,681,323 A | 10/1997 | Arick |
| 5,695,476 A | 12/1997 | Harris |
| 5,697,907 A | 12/1997 | Gaba |
| 5,700,250 A | 12/1997 | Erskine |
| 5,702,371 A | 12/1997 | Bierman |
| 5,704,920 A | 1/1998 | Gyure |
| 5,709,662 A | 1/1998 | Olive et al. |
| 5,714,225 A | 2/1998 | Hansen et al. |
| 5,738,641 A | 4/1998 | Watson et al. |
| 5,741,288 A | 4/1998 | Rife |
| 5,752,923 A | 5/1998 | Terwilliger |
| 5,807,316 A | 9/1998 | Teeple |
| 5,807,348 A | 9/1998 | Zinger et al. |
| 5,810,835 A | 9/1998 | Ryan et al. |
| 5,817,058 A | 10/1998 | Shaw |
| 5,820,598 A | 10/1998 | Gazza et al. |
| 5,827,236 A | 10/1998 | Takahashi |
| 5,833,666 A | 11/1998 | Davis et al. |
| 5,843,001 A | 12/1998 | Goldenberg |
| 5,848,990 A | 12/1998 | Cirelli et al. |
| 5,851,197 A | 12/1998 | Marano et al. |
| 5,858,001 A | 1/1999 | Tsals et al. |
| 5,865,806 A | 2/1999 | Howell |
| 5,899,886 A | 5/1999 | Cosme |
| 5,911,705 A | 6/1999 | Howell |
| 5,913,846 A | 6/1999 | Szabo |
| 5,916,199 A | 6/1999 | Miles |
| 5,919,167 A | 7/1999 | Mulhauser et al. |
| 5,919,170 A | 7/1999 | Woessner |
| 5,925,032 A | 7/1999 | Clements |
| 5,935,109 A | 8/1999 | Donnan |
| 5,947,931 A | 9/1999 | Bierman |
| 5,947,935 A | 9/1999 | Rhinehart et al. |
| 5,951,523 A | 9/1999 | Osterlind et al. |
| 5,954,643 A | 9/1999 | VanAntwerp et al. |
| 5,957,892 A | 9/1999 | Thorne |
| 5,957,897 A | 9/1999 | Jeffrey |
| 5,968,011 A | 10/1999 | Larsen et al. |
| 5,971,966 A | 10/1999 | Lav |
| 5,975,120 A | 11/1999 | Novosel |
| 5,980,488 A | 11/1999 | Thorne |
| 5,980,506 A | 11/1999 | Mathiasen |
| 5,984,224 A | 11/1999 | Yang |
| 5,984,897 A | 11/1999 | Peterson et al. |
| D417,733 S | 12/1999 | Howell et al. |
| 6,017,328 A * | 1/2000 | Fischell et al. .......... 604/180 |
| 6,017,598 A | 1/2000 | Kreischer et al. |
| D421,119 S | 2/2000 | Musgrave et al. |
| 6,024,727 A | 2/2000 | Thorne et al. |
| 6,039,629 A | 3/2000 | Mitchell |
| 6,042,570 A | 3/2000 | Bell et al. |
| 6,045,533 A | 4/2000 | Kriesel et al. |
| 6,045,534 A | 4/2000 | Jacobsen et al. |
| 6,050,976 A | 4/2000 | Thorne et al. |
| 6,053,893 A | 4/2000 | Bucher |
| 6,053,930 A | 4/2000 | Ruppert |
| 6,056,718 A | 5/2000 | Funderburk et al. |
| 6,056,726 A | 5/2000 | Isaacson |
| 6,074,369 A | 6/2000 | Sage et al. |
| 6,074,371 A | 6/2000 | Fischell |
| 6,077,244 A | 6/2000 | Botich et al. |
| 6,079,432 A | 6/2000 | Paradis |
| 6,086,008 A | 7/2000 | Gray et al. |
| 6,086,575 A | 7/2000 | Mejslov |
| 6,090,068 A | 7/2000 | Chanut |
| 6,093,172 A | 7/2000 | Funderburk et al. |
| 6,093,179 A | 7/2000 | O'Hara et al. |
| 6,099,503 A | 8/2000 | Stardella |
| 6,105,218 A | 8/2000 | Reekie |
| 6,106,498 A | 8/2000 | Friedli et al. |
| 6,120,482 A | 9/2000 | Szabo |
| 6,123,690 A | 9/2000 | Mejslov |
| 6,132,755 A | 10/2000 | Eicher et al. |
| 6,139,534 A | 10/2000 | Niedospial, Jr. |
| 6,159,181 A | 12/2000 | Crossman et al. |
| 6,183,464 B1 | 2/2001 | Sharp et al. |
| 6,191,338 B1 | 2/2001 | Haller |
| 6,193,694 B1 | 2/2001 | Bell et al. |
| 6,210,420 B1 | 4/2001 | Mauze et al. |
| 6,219,574 B1 | 4/2001 | Cormier et al. |
| 6,221,058 B1 | 4/2001 | Kao et al. |
| 6,248,093 B1 | 6/2001 | Moberg |
| 6,261,272 B1 | 7/2001 | Gross et al. |
| 6,293,925 B1 | 9/2001 | Safabash et al. |
| 6,302,866 B1 | 10/2001 | Marggi |
| 6,319,232 B1 | 11/2001 | Kashmer |
| 6,322,535 B1 | 11/2001 | Hitchins et al. |
| 6,322,808 B1 | 11/2001 | Trautman et al. |
| 6,334,856 B1 | 1/2002 | Allen et al. |
| 6,355,021 B1 | 3/2002 | Nielsen et al. |
| 6,364,113 B1 | 4/2002 | Faasse et al. |
| 6,378,218 B2 | 4/2002 | Sigwart et al. |
| 6,379,335 B1 | 4/2002 | Rigon et al. |
| 6,387,076 B1 | 5/2002 | Van Lunduyt |
| 6,387,078 B1 | 5/2002 | Gillespie, III |
| 6,405,876 B1 | 6/2002 | Seshimoto et al. |
| 6,440,096 B1 | 8/2002 | Lastovich et al. |
| 6,447,482 B1 | 9/2002 | Rønborg et al. |
| 6,450,992 B1 | 9/2002 | Cassidy, Jr. |
| 6,485,461 B1 | 11/2002 | Mason et al. |
| 6,488,663 B1 | 12/2002 | Steg |
| 6,503,222 B2 | 1/2003 | Lo |
| 6,517,517 B1 | 2/2003 | Farrugia et al. |
| 6,520,938 B1 | 2/2003 | Funderburk et al. |
| D472,316 S | 3/2003 | Douglas et al. |
| D472,630 S | 4/2003 | Douglas et al. |
| 6,572,586 B1 | 6/2003 | Wojcik |
| 6,579,267 B2 | 6/2003 | Lynch et al. |
| 6,582,397 B2 | 6/2003 | Alesi et al. |
| 6,595,962 B1 | 7/2003 | Perthu |
| 6,607,509 B2 | 8/2003 | Bobroff et al. |
| 6,607,511 B2 | 8/2003 | Bobroff et al. |
| 6,613,064 B2 | 9/2003 | Rutynowski et al. |
| 6,620,133 B1 | 9/2003 | Steck |
| 6,620,136 B1 | 9/2003 | Pressly, Sr. et al. |
| 6,620,140 B1 | 9/2003 | Metzger |
| 6,629,949 B1 | 10/2003 | Douglas |
| 6,645,181 B1 | 11/2003 | Gilad et al. |
| 6,645,182 B1 | 11/2003 | Szabo |
| 6,659,982 B2 | 12/2003 | Douglas et al. |
| 6,685,674 B2 | 2/2004 | Douglas et al. |
| 6,699,218 B2 | 3/2004 | Flaherty et al. |
| 6,702,779 B2 | 3/2004 | Connelly et al. |
| 6,726,649 B2 | 4/2004 | Swenson et al. |
| 6,736,797 B1 | 5/2004 | Larsen et al. |
| 6,743,203 B1 | 6/2004 | Pickhard |
| 6,749,587 B2 | 6/2004 | Flaherty |
| 6,749,589 B1 | 6/2004 | Douglas et al. |
| 6,755,805 B1 | 6/2004 | Reid |
| 6,776,775 B1 | 8/2004 | Mohammad |

(56) References Cited

U.S. PATENT DOCUMENTS

| | | |
|---|---|---|
| 6,790,199 B1 | 9/2004 | Gianakos |
| 6,805,686 B1 | 10/2004 | Fathallah et al. |
| 6,808,506 B2 | 10/2004 | Lastovich et al. |
| 6,811,545 B2 | 11/2004 | Vaillancourt |
| 6,814,720 B2 | 11/2004 | Olsen et al. |
| 6,824,530 B2 | 11/2004 | Wagner et al. |
| 6,824,531 B1 | 11/2004 | Zecha, Jr. et al. |
| 6,830,562 B2 | 12/2004 | Mogensen et al. |
| 6,837,877 B2 | 1/2005 | Zurcher |
| 6,837,878 B2 | 1/2005 | Smutney et al. |
| 6,840,922 B2 | 1/2005 | Nielsen et al. |
| 6,880,701 B2 | 4/2005 | Bergeron et al. |
| 6,923,791 B2 | 8/2005 | Douglas |
| 6,926,694 B2 | 8/2005 | Marano-Ford et al. |
| 6,939,324 B2 | 9/2005 | Gonnelli et al. |
| 6,939,331 B2 | 9/2005 | Ohshima |
| 6,949,084 B2 | 9/2005 | Marggi et al. |
| 6,959,812 B2 | 11/2005 | Reif et al. |
| 6,960,193 B2 | 11/2005 | Rosenberg |
| 6,979,316 B1 | 12/2005 | Rubin et al. |
| 6,991,619 B2 | 1/2006 | Marano-Ford et al. |
| 6,991,620 B2 | 1/2006 | Marano-Ford et al. |
| 6,994,213 B2 | 2/2006 | Giard et al. |
| 6,997,907 B2 | 2/2006 | Safabash et al. |
| 7,014,625 B2 | 3/2006 | Bengtsson |
| 7,018,344 B2 | 3/2006 | Bressler et al. |
| 7,022,108 B2 | 4/2006 | Marano-Ford et al. |
| 7,047,070 B2 | 5/2006 | Wilkenson et al. |
| 7,052,483 B2 | 5/2006 | Wojcik |
| 7,055,713 B2 | 6/2006 | Rea et al. |
| 7,056,302 B2 | 6/2006 | Douglas |
| 7,070,580 B2 * | 7/2006 | Nielsen .......... 604/180 |
| 7,074,208 B2 | 7/2006 | Pajunk et al. |
| D526,409 S | 8/2006 | Nielsen et al. |
| 7,083,592 B2 | 8/2006 | Lastovich et al. |
| 7,083,597 B2 | 8/2006 | Lynch et al. |
| 7,097,631 B2 | 8/2006 | Trautman et al. |
| 7,109,878 B2 | 9/2006 | Mann et al. |
| 7,115,108 B2 | 10/2006 | Wilkenson et al. |
| 7,115,112 B2 | 10/2006 | Mogensen et al. |
| 7,137,968 B1 | 11/2006 | Burrell et al. |
| 7,141,023 B2 | 11/2006 | Diermann et al. |
| 7,147,623 B2 | 12/2006 | Mathiasen |
| 7,186,236 B2 | 3/2007 | Gibson et al. |
| 7,211,068 B2 | 5/2007 | Douglas |
| 7,214,207 B2 | 5/2007 | Lynch et al. |
| 7,214,215 B2 | 5/2007 | Heinzerling et al. |
| 7,250,037 B2 | 7/2007 | Shermer et al. |
| 7,258,680 B2 | 8/2007 | Mogensen et al. |
| D554,253 S | 10/2007 | Kornerup |
| 7,303,543 B1 | 12/2007 | Maule et al. |
| 7,309,326 B2 | 12/2007 | Fangrow, Jr. |
| 7,322,473 B2 | 1/2008 | Fux |
| 7,331,939 B2 * | 2/2008 | Fangrow, Jr. ............ 604/167.02 |
| 7,407,491 B2 | 8/2008 | Fangrow, Jr. |
| 7,407,493 B2 | 8/2008 | Cane' |
| 7,431,876 B2 | 10/2008 | Mejlhede et al. |
| 7,441,655 B1 | 10/2008 | Hoftman |
| 7,569,262 B2 | 8/2009 | Szabo et al. |
| 7,621,395 B2 * | 11/2009 | Mogensen et al. .......... 206/365 |
| 7,648,494 B2 | 1/2010 | Kornerup et al. |
| 7,713,258 B2 * | 5/2010 | Adams et al. .............. 604/513 |
| 7,766,867 B2 | 8/2010 | Lynch et al. |
| 7,846,132 B2 | 12/2010 | Gravesen et al. |
| 7,850,652 B2 | 12/2010 | Liniger et al. |
| 8,012,126 B2 | 9/2011 | Tipsmark et al. |
| 8,087,333 B2 | 1/2012 | Oishi |
| 8,123,724 B2 | 2/2012 | Gillespie, III |
| 8,303,549 B2 | 11/2012 | Mejlhede et al. |
| 8,323,250 B2 | 12/2012 | Chong et al. |
| 2001/0004970 A1 | 6/2001 | Hollister et al. |
| 2001/0016714 A1 | 8/2001 | Bell et al. |
| 2001/0021827 A1 | 9/2001 | Ferguson et al. |
| 2001/0039387 A1 | 11/2001 | Rutynowski et al. |
| 2001/0039401 A1 | 11/2001 | Ferguson et al. |
| 2001/0041875 A1 | 11/2001 | Higuchi et al. |
| 2001/0049496 A1 | 12/2001 | Kirchhofer |
| 2001/0053889 A1 | 12/2001 | Marggi |
| 2001/0056284 A1 | 12/2001 | Purcell et al. |
| 2002/0022798 A1 | 2/2002 | Connelly |
| 2002/0022855 A1 | 2/2002 | Bobroff et al. |
| 2002/0026152 A1 | 2/2002 | Bierman |
| 2002/0055711 A1 | 5/2002 | Lavi et al. |
| 2002/0068904 A1 | 6/2002 | Pluth et al. |
| 2002/0072720 A1 | 6/2002 | Hague et al. |
| 2002/0074345 A1 | 6/2002 | Scheider et al. |
| 2002/0077599 A1 | 6/2002 | Wojcik |
| 2002/0082543 A1 | 6/2002 | Park et al. |
| 2002/0107489 A1 | 8/2002 | Lee |
| 2002/0111581 A1 | 8/2002 | Sasso |
| 2002/0156424 A1 | 10/2002 | Suzuki et al. |
| 2002/0156427 A1 | 10/2002 | Suzuki et al. |
| 2002/0161322 A1 | 10/2002 | Utterberg et al. |
| 2002/0161332 A1 | 10/2002 | Ramey |
| 2002/0161386 A1 | 10/2002 | Halseth et al. |
| 2002/0165493 A1 | 11/2002 | Bierman |
| 2002/0169419 A1 | 11/2002 | Steg |
| 2002/0173748 A1 | 11/2002 | McConnell et al. |
| 2002/0173769 A1 | 11/2002 | Gray et al. |
| 2002/0183688 A1 | 12/2002 | Lastovich et al. |
| 2002/0189688 A1 | 12/2002 | Roorda |
| 2002/0193737 A1 | 12/2002 | Popovsky |
| 2002/0193744 A1 | 12/2002 | Alesi et al. |
| 2003/0014018 A1 | 1/2003 | Giambattista et al. |
| 2003/0060781 A1 | 3/2003 | Mogensen et al. |
| 2003/0069548 A1 | 4/2003 | Connelly et al. |
| 2003/0088238 A1 | 5/2003 | Poulsen et al. |
| 2003/0105430 A1 | 6/2003 | Lavi et al. |
| 2003/0109829 A1 | 6/2003 | Mogensen et al. |
| 2003/0125669 A1 | 7/2003 | Safabash et al. |
| 2003/0125678 A1 | 7/2003 | Swenson et al. |
| 2003/0130619 A1 | 7/2003 | Safabash et al. |
| 2003/0139704 A1 | 7/2003 | Lin |
| 2003/0158520 A1 | 8/2003 | Safabash et al. |
| 2003/0176843 A1 | 9/2003 | Wilkinson |
| 2003/0176852 A1 | 9/2003 | Lynch et al. |
| 2003/0181863 A1 | 9/2003 | Davis et al. |
| 2003/0181868 A1 | 9/2003 | Swenson |
| 2003/0181873 A1 | 9/2003 | Swenson |
| 2003/0181874 A1 | 9/2003 | Bressler et al. |
| 2003/0187394 A1 | 10/2003 | Wilkinson et al. |
| 2003/0187395 A1 | 10/2003 | Gabel |
| 2003/0199823 A1 | 10/2003 | Bobroff et al. |
| 2003/0216686 A1 | 11/2003 | Lynch et al. |
| 2003/0220610 A1 | 11/2003 | Lastovich et al. |
| 2003/0225373 A1 | 12/2003 | Bobroff et al. |
| 2003/0225374 A1 | 12/2003 | Mathiasen |
| 2003/0229308 A1 | 12/2003 | Tsals et al. |
| 2003/0229316 A1 | 12/2003 | Hwang et al. |
| 2004/0002682 A1 | 1/2004 | Kovelman et al. |
| 2004/0006316 A1 | 1/2004 | Patton |
| 2004/0044306 A1 | 3/2004 | Lynch et al. |
| 2004/0049159 A1 | 3/2004 | Barrus et al. |
| 2004/0055711 A1 | 3/2004 | Martin et al. |
| 2004/0059316 A1 | 3/2004 | Smedegaard |
| 2004/0068231 A1 | 4/2004 | Blondeau |
| 2004/0069044 A1 | 4/2004 | Lavi et al. |
| 2004/0087913 A1 | 5/2004 | Rogers et al. |
| 2004/0092865 A1 | 5/2004 | Flaherty et al. |
| 2004/0092875 A1 | 5/2004 | Kochamba |
| 2004/0111068 A1 | 6/2004 | Swenson |
| 2004/0112781 A1 | 6/2004 | Hofverberg et al. |
| 2004/0116865 A1 | 6/2004 | Bengtsson |
| 2004/0133164 A1 | 7/2004 | Funderburk et al. |
| 2004/0138612 A1 | 7/2004 | Shermer et al. |
| 2004/0138620 A1 | 7/2004 | Douglas et al. |
| 2004/0143216 A1 | 7/2004 | Douglas et al. |
| 2004/0143218 A1 | 7/2004 | Das |
| 2004/0158202 A1 | 8/2004 | Jensen |
| 2004/0158207 A1 | 8/2004 | Hunn et al. |
| 2004/0162518 A1 | 8/2004 | Connelly et al. |
| 2004/0162521 A1 * | 8/2004 | Bengtsson .................. 604/136 |
| 2004/0171989 A1 | 9/2004 | Horner et al. |
| 2004/0178098 A1 | 9/2004 | Swenson et al. |

(56) References Cited

U.S. PATENT DOCUMENTS

| | | |
|---|---|---|
| 2004/0186446 A1 | 9/2004 | Ohshima |
| 2004/0193143 A1 | 9/2004 | Sauer |
| 2004/0199123 A1* | 10/2004 | Nielsen .................. 604/180 |
| 2004/0204673 A1 | 10/2004 | Flaherty et al. |
| 2004/0204687 A1* | 10/2004 | Mogensen et al. ........... 604/181 |
| 2004/0204690 A1 | 10/2004 | Yashiro et al. |
| 2004/0215151 A1 | 10/2004 | Marshall et al. |
| 2004/0220528 A1 | 11/2004 | Garcia, Jr. |
| 2004/0236284 A1 | 11/2004 | Hoste et al. |
| 2004/0238392 A1 | 12/2004 | Peterson et al. |
| 2004/0243065 A1 | 12/2004 | McConnell et al. |
| 2004/0254433 A1 | 12/2004 | Bandis et al. |
| 2004/0260235 A1 | 12/2004 | Douglas |
| 2004/0260250 A1 | 12/2004 | Harris et al. |
| 2005/0035014 A1 | 2/2005 | Cane |
| 2005/0038378 A1 | 2/2005 | Lastovich et al. |
| 2005/0043687 A1* | 2/2005 | Mogensen et al. ........... 604/181 |
| 2005/0049571 A1 | 3/2005 | Lastovich et al. |
| 2005/0065466 A1 | 3/2005 | Vedrine |
| 2005/0065472 A1 | 3/2005 | Cindrich et al. |
| 2005/0075606 A1 | 4/2005 | Botich et al. |
| 2005/0080386 A1 | 4/2005 | Reid |
| 2005/0101910 A1 | 5/2005 | Bowman et al. |
| 2005/0101912 A1 | 5/2005 | Faust et al. |
| 2005/0101932 A1 | 5/2005 | Cote et al. |
| 2005/0101933 A1 | 5/2005 | Marrs et al. |
| 2005/0107743 A1 | 5/2005 | Fangrow, Jr. |
| 2005/0113761 A1 | 5/2005 | Faust et al. |
| 2005/0119611 A1 | 6/2005 | Marano-Ford et al. |
| 2005/0119619 A1 | 6/2005 | Haining |
| 2005/0119637 A1 | 6/2005 | Lundgren et al. |
| 2005/0124936 A1* | 6/2005 | Mogensen et al. ........... 604/136 |
| 2005/0131347 A1 | 6/2005 | Marano-Ford et al. |
| 2005/0159709 A1 | 7/2005 | Wilkinson |
| 2005/0159714 A1 | 7/2005 | Gibson |
| 2005/0165382 A1 | 7/2005 | Fulford |
| 2005/0192560 A1 | 9/2005 | Walls et al. |
| 2005/0203461 A1 | 9/2005 | Flaherty et al. |
| 2005/0215979 A1 | 9/2005 | Kornerup et al. |
| 2005/0240154 A1 | 10/2005 | Mogensen et al. |
| 2005/0251098 A1 | 11/2005 | Wyss et al. |
| 2005/0256456 A1 | 11/2005 | Marano-Ford et al. |
| 2005/0261629 A1 | 11/2005 | Marano-Ford et al. |
| 2005/0277892 A1 | 12/2005 | Chen |
| 2005/0283114 A1 | 12/2005 | Bresina et al. |
| 2006/0015063 A1 | 1/2006 | Butikofer et al. |
| 2006/0015076 A1 | 1/2006 | Heinzerling et al. |
| 2006/0030815 A1 | 2/2006 | Csincsura et al. |
| 2006/0036214 A1 | 2/2006 | Mogensen et al. |
| 2006/0041224 A1 | 2/2006 | Jensen |
| 2006/0069351 A9 | 3/2006 | Safabash et al. |
| 2006/0069382 A1 | 3/2006 | Pedersen |
| 2006/0069383 A1 | 3/2006 | Bogaerts et al. |
| 2006/0095003 A1 | 5/2006 | Marano-Ford et al. |
| 2006/0095014 A1 | 5/2006 | Ethelfeld |
| 2006/0106346 A1 | 5/2006 | Sullivan et al. |
| 2006/0129123 A1 | 6/2006 | Wojcik |
| 2006/0135908 A1 | 6/2006 | Liniger et al. |
| 2006/0135913 A1 | 6/2006 | Ethelfeld |
| 2006/0142698 A1 | 6/2006 | Ethelfeld |
| 2006/0161108 A1 | 7/2006 | Mogensen et al. |
| 2006/0173410 A1 | 8/2006 | Moberg et al. |
| 2006/0173413 A1 | 8/2006 | Fan |
| 2006/0184104 A1 | 8/2006 | Cheney, II et al. |
| 2006/0184140 A1 | 8/2006 | Okiyama |
| 2006/0200073 A1 | 9/2006 | Radmer et al. |
| 2006/0241551 A1 | 10/2006 | Lynch et al. |
| 2006/0247553 A1 | 11/2006 | Diermann et al. |
| 2006/0247574 A1 | 11/2006 | Maule et al. |
| 2006/0253085 A1 | 11/2006 | Geismar et al. |
| 2006/0253086 A1 | 11/2006 | Moberg et al. |
| 2006/0264835 A1 | 11/2006 | Nielsen et al. |
| 2006/0264890 A1 | 11/2006 | Moberg et al. |
| 2007/0005017 A1 | 1/2007 | Alchas et al. |
| 2007/0016129 A1 | 1/2007 | Liniger et al. |
| 2007/0016159 A1 | 1/2007 | Sparholt et al. |
| 2007/0021729 A1 | 1/2007 | Mogensen et al. |
| 2007/0049865 A1 | 3/2007 | Radmer et al. |
| 2007/0049870 A1 | 3/2007 | Gray et al. |
| 2007/0051784 A1 | 3/2007 | Money et al. |
| 2007/0066955 A1 | 3/2007 | Sparholt et al. |
| 2007/0066958 A1 | 3/2007 | Wright |
| 2007/0088271 A1 | 4/2007 | Richards et al. |
| 2007/0093754 A1 | 4/2007 | Mogensen |
| 2007/0104596 A1 | 5/2007 | Preuthun et al. |
| 2007/0112301 A1 | 5/2007 | Preuthun et al. |
| 2007/0112303 A1 | 5/2007 | Liniger |
| 2007/0129688 A1 | 6/2007 | Scheurer et al. |
| 2007/0129691 A1 | 6/2007 | Sage, Jr. et al. |
| 2007/0173767 A1 | 7/2007 | Lynch et al. |
| 2007/0179444 A1 | 8/2007 | Causey et al. |
| 2007/0185441 A1 | 8/2007 | Fangrow, Jr. |
| 2007/0191772 A1 | 8/2007 | Wojcik |
| 2007/0191773 A1 | 8/2007 | Wojcik |
| 2007/0203454 A1 | 8/2007 | Shermer et al. |
| 2007/0213673 A1 | 9/2007 | Douglas |
| 2007/0244448 A1 | 10/2007 | Lastovich et al. |
| 2007/0282269 A1 | 12/2007 | Carter et al. |
| 2007/0299409 A1 | 12/2007 | Whitbourne et al. |
| 2008/0058692 A1 | 3/2008 | Propp et al. |
| 2008/0200897 A1 | 8/2008 | Hoss et al. |
| 2008/0269687 A1 | 10/2008 | Chong |
| 2008/0312601 A1 | 12/2008 | Cane' |
| 2009/0062767 A1 | 3/2009 | Van Antwerp et al. |
| 2009/0326456 A1 | 12/2009 | Cross et al. |
| 2010/0004597 A1 | 1/2010 | Gyrn et al. |
| 2010/0022956 A1 | 1/2010 | Tipsmark et al. |
| 2010/0137829 A1 | 6/2010 | Nielsen et al. |
| 2010/0228226 A1 | 9/2010 | Nielsen |
| 2010/0262078 A1 | 10/2010 | Blomquist |
| 2011/0054399 A1 | 3/2011 | Chong et al. |

FOREIGN PATENT DOCUMENTS

| | | |
|---|---|---|
| DE | 299 05 072 U1 | 9/1999 |
| DE | 101 17 285 A1 | 11/2002 |
| DE | 203 20 207 U1 | 11/2004 |
| EP | 0177632 B1 | 9/1984 |
| EP | 0 239 244 A1 | 9/1987 |
| EP | 0272530 A2 | 6/1988 |
| EP | 0451040 A1 | 10/1991 |
| EP | 0544837 B1 | 6/1993 |
| EP | 0615768 A2 | 9/1994 |
| EP | 0651662 B1 | 5/1995 |
| EP | 0652027 A1 | 5/1995 |
| EP | 0657184 A1 | 6/1995 |
| EP | 0688232 B1 | 12/1995 |
| EP | 0714631 B1 | 6/1996 |
| EP | 0744183 A2 | 11/1996 |
| EP | 0747006 A1 | 12/1996 |
| EP | 0799626 A1 | 10/1997 |
| EP | 0937475 A2 | 8/1999 |
| EP | 0956879 A1 | 11/1999 |
| EP | 2272559 A1 | 1/2001 |
| EP | 1086718 A1 | 3/2001 |
| EP | 1125593 A1 | 8/2001 |
| EP | 0775501 B1 | 6/2002 |
| EP | 1329233 A1 | 7/2003 |
| EP | 1350537 A1 | 10/2003 |
| EP | 1360970 A1 | 11/2003 |
| EP | 1380315 A1 | 1/2004 |
| EP | 1407747 A1 | 4/2004 |
| EP | 1407793 A1 | 4/2004 |
| EP | 1421968 A2 | 5/2004 |
| EP | 1177802 B1 | 9/2004 |
| EP | 1475113 A1 | 11/2004 |
| EP | 1495775 A1 | 1/2005 |
| EP | 1502613 A1 | 2/2005 |
| EP | 1525873 A1 | 4/2005 |
| EP | 1527792 A1 | 5/2005 |
| EP | 1559442 A2 | 8/2005 |
| EP | 1616594 A1 | 1/2006 |
| EP | 1704889 A1 | 9/2006 |
| EP | 1719537 A2 | 11/2006 |

(56) References Cited

FOREIGN PATENT DOCUMENTS

| | | |
|---|---|---|
| EP | 1762259 A1 | 3/2007 |
| EP | 1764125 A1 | 3/2007 |
| EP | 1776980 A1 | 4/2007 |
| EP | 1970091 A1 | 9/2008 |
| FR | 2725902 A1 | 10/1994 |
| FR | 2 752 164 A1 | 2/1998 |
| GB | 906574 | 9/1962 |
| GB | 2 088 215 A | 6/1982 |
| GB | 2 230 702 A | 10/1990 |
| GB | 2 423 267 A | 8/2006 |
| GB | 2 450 872 A | 7/2007 |
| GB | 2 459 101 A | 10/2009 |
| JP | 10179734 A | 8/1991 |
| JP | 7051251 A | 11/1995 |
| JP | 8187286 A | 7/1996 |
| JP | A-03-191965 A | 7/1998 |
| JP | 2002-028246 A | 1/2002 |
| RU | 2 238 111 C2 | 12/2003 |
| SU | 993 100 | 6/1982 |
| WO | WO 81/01795 A1 | 7/1981 |
| WO | WO 82/03558 A1 | 10/1982 |
| WO | WO 92/04062 A1 | 3/1992 |
| WO | WO 93/05840 A2 | 4/1993 |
| WO | WO 93/11709 A1 | 6/1993 |
| WO | WO 94/20160 A1 | 9/1994 |
| WO | WO 95/19194 A1 | 7/1995 |
| WO | WO 96/32981 A1 | 7/1996 |
| WO | WO 96/20021 A1 | 10/1996 |
| WO | WO 98/26835 A1 | 6/1998 |
| WO | WO 98/33549 A1 | 8/1998 |
| WO | WO 98/58693 A1 | 12/1998 |
| WO | WO 99/07435 A1 | 2/1999 |
| WO | WO99/22789 A1 | 5/1999 |
| WO | WO 99/33504 A1 | 7/1999 |
| WO | WO 00/02614 A1 | 1/2000 |
| WO | WO 00/03757 A1 | 1/2000 |
| WO | WO 00/44324 A1 | 8/2000 |
| WO | WO 01/12746 A1 | 2/2001 |
| WO | WO 01/30419 A2 | 5/2001 |
| WO | WO 01/68180 A1 | 9/2001 |
| WO | WO 01/72353 A2 | 10/2001 |
| WO | WO 01/76684 A1 | 10/2001 |
| WO | WO 01/93926 A2 | 12/2001 |
| WO | WO 02/02165 A2 | 1/2002 |
| WO | WO 02/07804 A1 | 1/2002 |
| WO | WO 02/40083 A2 | 5/2002 |
| WO | WO 02/053220 A2 | 7/2002 |
| WO | WO 02/081012 A2 | 10/2002 |
| WO | WO 02/081013 A2 | 10/2002 |
| WO | WO 02/083206 A2 | 10/2002 |
| WO | WO 02/083228 A2 | 10/2002 |
| WO | WO 02/094352 A2 | 11/2002 |
| WO | WO 02/100457 A2 | 12/2002 |
| WO | WO 02/102442 A1 | 12/2002 |
| WO | WO 02/068014 A3 | 1/2003 |
| WO | WO 03/015860 A1 | 2/2003 |
| WO | WO 03/026728 A1 | 4/2003 |
| WO | WO 03/068305 A1 | 8/2003 |
| WO | WO 03/075980 A2 | 9/2003 |
| WO | WO 03/095003 A1 | 11/2003 |
| WO | WO 2004/012796 A1 | 2/2004 |
| WO | WO 2004/024219 A1 | 3/2004 |
| WO | WO 2004/026375 A1 | 4/2004 |
| WO | WO 2004/029457 A1 | 4/2004 |
| WO | WO 2004/030726 A1 | 4/2004 |
| WO | WO 2004/037325 A1 | 5/2004 |
| WO | WO 2004/054644 A1 | 7/2004 |
| WO | WO 2004/056412 A2 | 7/2004 |
| WO | WO 2004/064593 A2 | 8/2004 |
| WO | WO 2004/071308 A1 | 8/2004 |
| WO | WO 2004/087240 A1 | 10/2004 |
| WO | WO 2004/098683 A1 | 11/2004 |
| WO | WO 2004/101016 A1 | 11/2004 |
| WO | WO 2004/101071 A2 | 11/2004 |
| WO | WO 2004/110527 A1 | 12/2004 |
| WO | WO 2005/002649 A1 | 1/2005 |
| WO | WO 2005/004973 A1 | 1/2005 |
| WO | WO 2005/018703 A2 | 3/2005 |
| WO | WO 2005/037184 A2 | 4/2005 |
| WO | WO 2005/037350 A2 | 4/2005 |
| WO | WO 2005/039673 A2 | 5/2005 |
| WO | WO 2005/046780 A1 | 5/2005 |
| WO | WO 2005/065748 A1 | 7/2005 |
| WO | WO 2005/068006 A1 | 7/2005 |
| WO | WO 2005/072795 A2 | 8/2005 |
| WO | WO 2005/092410 A1 | 10/2005 |
| WO | WO 2005/094920 A1 | 10/2005 |
| WO | WO 2005/112800 A2 | 12/2005 |
| WO | WO 2005/118055 A1 | 12/2005 |
| WO | WO 2006/003130 A1 | 1/2006 |
| WO | WO 2006/015507 A1 | 2/2006 |
| WO | WO 2006/015600 A2 | 2/2006 |
| WO | WO 2006/024650 A2 | 3/2006 |
| WO | WO 2006/032689 A1 | 3/2006 |
| WO | WO 2006/032692 A1 | 3/2006 |
| WO | WO 2006/061027 A2 | 6/2006 |
| WO | WO 2006/061354 A1 | 6/2006 |
| WO | WO 2006/062680 A1 | 6/2006 |
| WO | WO 2006/062912 A1 | 6/2006 |
| WO | WO 2006/075016 A1 | 7/2006 |
| WO | WO 2006/077262 A1 | 7/2006 |
| WO | WO 2006/077263 A1 | 7/2006 |
| WO | WO 2006/089958 A1 | 8/2006 |
| WO | WO 2006/097111 A2 | 9/2006 |
| WO | WO 2006/108775 A2 | 10/2006 |
| WO | WO 2006/120253 A2 | 11/2006 |
| WO | WO 2006/121921 A2 | 11/2006 |
| WO | WO 2006/122048 A1 | 11/2006 |
| WO | WO 2007/000162 A2 | 1/2007 |
| WO | WO 2007/002523 A2 | 1/2007 |
| WO | WO 2007/020090 A1 | 2/2007 |
| WO | WO 2007/065944 A1 | 6/2007 |
| WO | WO 2007/071255 A1 | 6/2007 |
| WO | WO 2007/071258 A1 | 6/2007 |
| WO | WO 2007/093051 A1 | 8/2007 |
| WO | WO 2007/093182 A2 | 8/2007 |
| WO | WO 2007/122207 A1 | 11/2007 |
| WO | WO 2007/140631 A1 | 12/2007 |
| WO | WO 2007/140783 A1 | 12/2007 |
| WO | WO 2007/140785 A1 | 12/2007 |
| WO | WO 2007/141210 A1 | 12/2007 |
| WO | WO 2008/014791 A1 | 2/2008 |
| WO | WO 2008/014792 A1 | 2/2008 |
| WO | WO 2008/048631 A1 | 4/2008 |
| WO | WO 2008/052545 A1 | 5/2008 |
| WO | WO 2008/065646 A1 | 6/2008 |
| WO | WO 2008/092782 A1 | 8/2008 |
| WO | WO 2008/092958 A1 | 8/2008 |
| WO | WO 2008/092959 A1 | 8/2008 |
| WO | WO 2008/133702 A1 | 11/2008 |
| WO | WO 2008/135098 A1 | 11/2008 |
| WO | WO 2008/147600 A1 | 12/2008 |
| WO | WO 2008/148714 A1 | 12/2008 |
| WO | WO 2008/155145 A1 | 12/2008 |
| WO | WO 2008/155377 A1 | 12/2008 |
| WO | WO 2009/004026 A1 | 1/2009 |
| WO | WO 2009/007287 A1 | 1/2009 |
| WO | WO 2009/010396 A1 | 1/2009 |
| WO | WO 2009/010399 A1 | 1/2009 |
| WO | WO 2009/016635 A2 | 2/2009 |
| WO | WO 2009/033032 A1 | 3/2009 |
| WO | WO 2009/039013 A1 | 3/2009 |
| WO | WO 2009/098291 A1 | 8/2009 |
| WO | WO 2009/098306 A1 | 8/2009 |
| WO | WO 2009/101130 A1 | 8/2009 |
| WO | WO 2009/101145 A1 | 8/2009 |
| WO | WO 2009/103759 A1 | 8/2009 |
| WO | WO 2009/106517 A1 | 9/2009 |
| WO | WO 2009/144272 A1 | 12/2009 |
| WO | WO 2010/003885 A1 | 1/2010 |
| WO | WO 2010/003886 A1 | 1/2010 |
| WO | WO 2010/030602 A1 | 3/2010 |
| WO | WO 2010/034830 A1 | 4/2010 |
| WO | WO 2010/072664 A1 | 7/2010 |

(56) References Cited

FOREIGN PATENT DOCUMENTS

| WO | WO 2010/080715 A1 | 7/2010 |
| WO | WO 2010/112521 A1 | 10/2010 |
| WO | WO 2011/012465 A1 | 2/2011 |
| WO | WO 2011/015659 A1 | 2/2011 |
| WO | WO 2011/121023 A1 | 10/2011 |
| WO | WO 2012/041784 A1 | 4/2012 |
| WO | WO 2012/041923 A2 | 4/2012 |
| WO | WO 2012/045667 A2 | 4/2012 |

\* cited by examiner

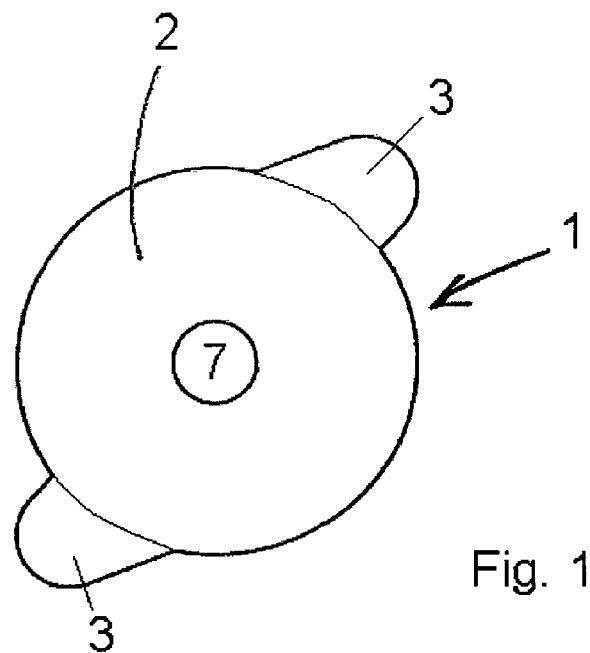
Fig. 1
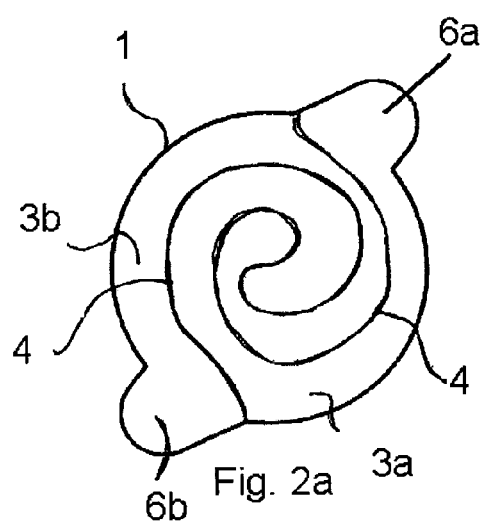
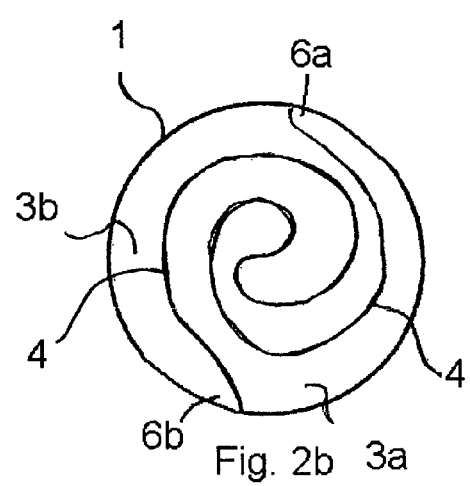

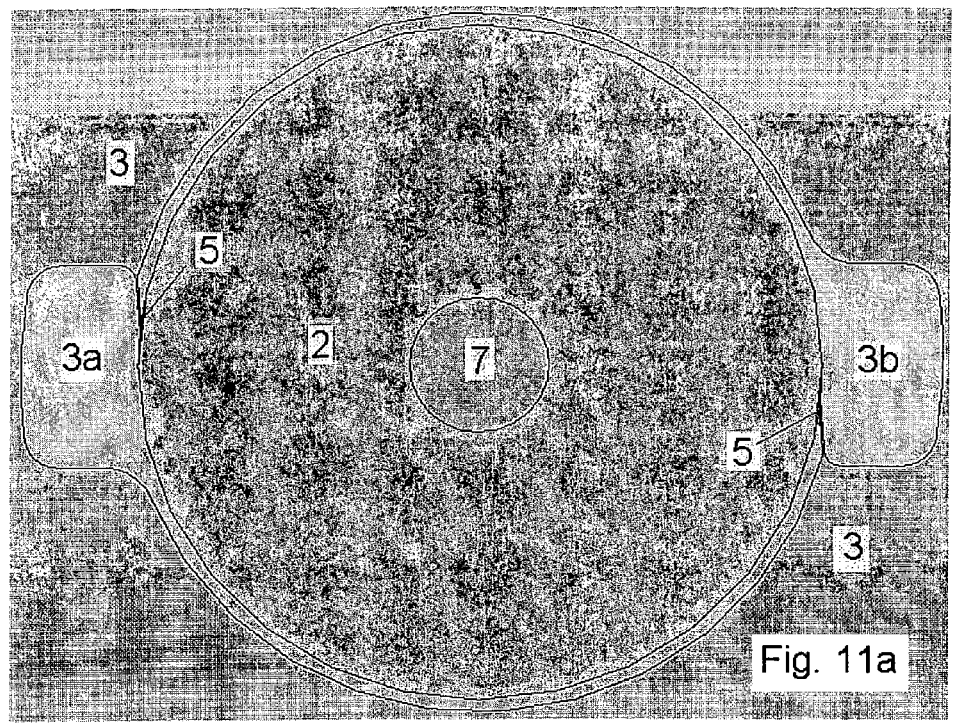
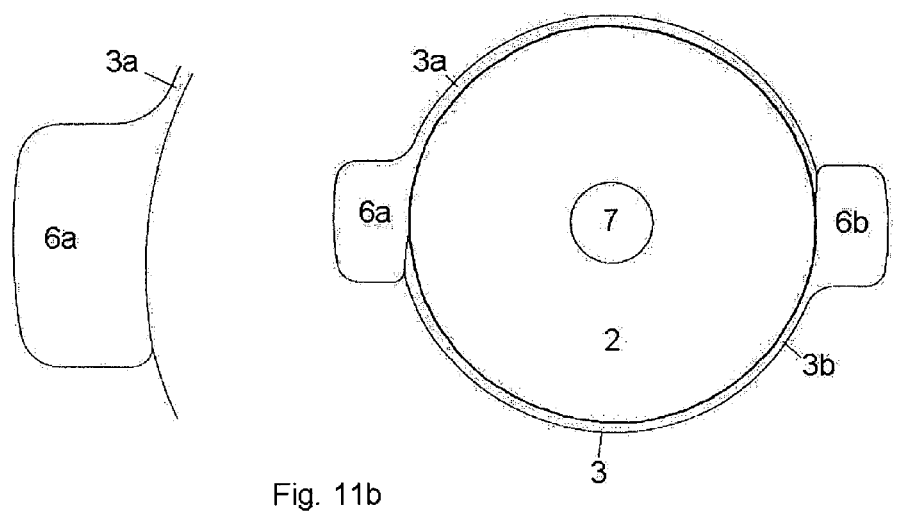
Fig. 11b

MOUNTING PAD

This application claims the benefit under 35 U.S.C. §371 of International Application No. PCT/DK2007/000278, filed Jun. 8, 2007, which claims the benefit of Danish Patent Application No. PA 2006 00779, filed Jun. 9, 2006, U.S. Provisional Application Ser. No. 60/812,469, filed Jun. 9, 2006, and U.S. Provisional Application Ser. No. 60/876,689, filed Dec. 22, 2006. These references are incorporated herein in their entirety.

FIELD OF INVENTION

The invention relates to a mounting pad comprising an adhesive layer which is being provided with a removable release liner for use in devices applied onto the skin of a patient, particular infusion devices. The invention also relates to a cannula device including a mounting pad comprising an adhesive layer which is being provided with a release liner which can be automatically removed from the mounting pad when the infusion set is applied to a patient. Furthermore, the invention relates to a method for removing a release liner from a mounting pad. Still further, the invention relates to the use of such a mounting pad.

BACKGROUND OF THE INVENTION

U.S. Pat. No. 5,384,174 A describes an adhesive pad for use on the skin, said adhesive pad comprising a release liner, which release liner is removed prior to application of the pad on the skin. The release liner may be one single piece or is provided with score lines or perforations, such that the release liner is divided into two or more sections, such that the release liner may be removed from the adhesive device in two or more pieces.

EP 0239244 A1 describes an injection set for subcutaneous delivery of a fluid to a patient, the injection set being provided with an adhesive sheet comprising a backing layer, an adhesive layer and a removable release liner. The release liner comprises a radial score line starting at the periphery of the release liner and ending on the border of the periphery of a central aperture of the release liner. The release liner is removed manually in one piece before applying the infusion set to the patient.

WO 00/44324 A1 describes an adhesive pad covered by a removable release paper having one or more pre-cut or pre-score lines, and the pre-cut score lines extending as straight lines from the periphery of the release paper inwardly towards the centre of the release paper. The adhesive pad and the removable release paper may have an aperture accommodating a stoma.

With the above mentioned types of products there is a risk that during removal of the release line the adhesive layer will become contaminated by accidental touches by the user. Furthermore, there is a risk of reducing its ability to adhere to the skin. Further, with the known products it can also be difficult to remove all of the release liner without tearing of the liner material, especially in the cases where the release liner is in one piece. Still further, the pull required must be even or smooth in order not to break the release liner during the pull thereby leaving remains of the release liner on the adhesive surface.

International application WO 04/087240 A1 teaches an injection device for placement on the skin of a user and from which a medical fluid such as insulin is injected via a cannula into the user, as the injection device includes a subcutaneous infusion set. The infusion device can be adhered to the skin of the user by means of an adhesive pad that is connected to the lower face of the infusion device and with its adhesive face facing towards the skin of the user. Upon penetration of the skin and subsequent activation of means in the injection device, injection is performed of the medical fluid such as insulin. The release liner covering the adhesive pad is provided with one score line which forms the release liner as a single strip in the form of a spiral.

Scoring the release liner as a long narrow strip gives an even pull and small force is needed to remove the spiral shaped release liner since all it takes is to overcome the adhesive force of the piece of strip being peeled by the user.

However, scoring the release liner as a single strip e.g. in the form as a spiral means that the strip as well as the pull-length becomes relatively long during removal of the release liner before the entire release liner is removed from the adhesive pad.

It is the object of the invention to remedy the above-identified problems and to provide an alternative mounting pad that can be used either alone or in combination with an infusion device, said mounting pad having an easily removable release liner, which can be removed in a single upwardly directed straight movement of the hand, thereby reducing the risk of the user handling the product erroneously. Further, it is an object to use little force in removing the release liner and at the same time to reduce the pull-length during removal of the release liner to get at more straight and upwardly directed movement of the hand.

Moreover, it is an object of the invention to provide an infusion set which is rapid and easy to apply to a patient.

It is further an object of the invention to provide an easy method of removing a release liner from a mounting pad without contaminating or damaging the adhering effect of the mounting pad.

SUMMARY OF THE INVENTION

The present invention relates to a mounting pad comprising an adhesive layer, said layer being provided with a removable release liner, said release liner being divided into at least two sections wherein each of the at least two said sections of the release liner is provided with one or more score lines thereby forming each section of the release liner as a strip.

One end of each section of the release line is provided with means for fastening this one end to an opposite positioned surface. The means referred to could e.g. be a surface having characteristics which makes the surface suitable for adhering to an adhesive placed on the opposite positioned surface or the means could e.g. be of a mechanical kind which can fasten the release liner to the opposite positioned surface.

In a second aspect the invention relates to a cannula device for subcutaneous introduction of a cannula, the cannula device comprising a housing with an upper face plate and a lower face plate and a cannula connected to the lower face plate and a mounting pad placed in connection with the lower face plate and for securing the cannula device to the skin; said mounting pad comprising an adhesive layer being provided with a removable release liner, said release liner being divided into at least two sections and wherein each of the at least two sections of the release liner is provided with one or more score lines thereby forming each section of the release liner as a strip.

The present invention renders it possible by a single straight upward pull to peel a release liner in two or more narrow strips, thereby still maintaining an even pull with little force needed to remove the release liner. Further, the pull-length of the release liner is reduced as the release liner is divided into two or more strips, which is removed simultaneously by the single straight upward pull.

Furthermore, the handling is easy and tearing of the release liner can be avoided. The handling will take place in the same manner as in case the mounting pad is used without an injection device.

In a third aspect the invention relates to a method of removing a release liner from a mounting pad comprising retaining a point of each section of the release liner in the periphery of the mounting pad, removing the release liner by pulling in a single straight pull.

The method of the invention renders it possible to remove the release liner in a single upwardly directed straight movement of the hand, thereby reducing the risk of the user handling the product erroneously. Further, the method of the invention renders it possible to use a small force in removing the release liner and at the same time to reduce the pull-length during removal of the release liner thereby getting a straighter and upwardly directed movement of the hand. Still further, the method of the invention reduces the risk of accidental touch of the adhesive layer by which the ability to adhere to the skin and the risk of subsequently contamination of the skin is reduced.

In a fourth aspect the invention relates to the use of a mounting pad comprising an adhesive layer, said layer being provided with a removable release liner, said release liner being divided into at least two sections wherein each of the at least two said sections of the release liner is provided with one or more score lines thereby defining each section of the release liner as a strip in a cannula device for subcutaneous introduction of a cannula comprising a housing with an upper face plate and a lower face plate and a cannula connected to the lower face plate wherein the mounting pad is placed in connection with the lower face plate and for securing the cannula device to the skin.

DEFINITIONS

The term "mounting pad" as used herein designates an adhesive component having an adhesive layer covered with a release liner, where the mounting pad is for securing a medical device such as a wound dressing, an ostomy appliance or for fixation of a cannula device or an infusion set for injection of insulin in a patient to the skin of a patient.

The term "release liner" as used herein designates a non-adhesive protective layer, which protects the adhesive surface of the mounting pad before use.

The release liner covers essentially the entire adhesive surface and can also extend beyond the boundaries of the mounting pad forming extensions or tabs projecting beyond the boundaries of the mounting pad. The projections facilitate gripping the release liner for removal thereof or securing the same to an application device.

The term "pull-length" as used herein designates a pulling distance which is needed for completely removing the release liner from the adhesive surface.

The term "cannula device" as used herein generally designates a device for the subcutaneous introduction of a cannula of an infusion part of an infusion set or a transcutaneous sensor known per se into the skin of a patient.

The term "infusion set" as used herein in the present context designates a set known per se comprising an infusion part provided with a cannula to penetrate the skin of a user and a connector for connecting the infusion part with a medical device such as an insulin pump. An infusion set has in its assembled form a substantially planar rear side.

The term "projecting part" as used herein designates a part of a release liner or an adhesive surface protruding from the periphery thereof.

The term "score line" as used herein designates a weakening line wherein forces required for breaking the release liner is lower e.g. in the form of a perforated line, a cut-out line or a full score line.

The term "strip" as used herein designates an object shaped with a first end and a second end, such as a ribbon, a band, a half-circle, helix etc.

SHORT DESCRIPTION OF THE DRAWINGS

The invention will now be explained in further detail with reference to the drawing, wherein:

FIG. 1 shows an embodiment of a mounting pad according to the invention;

FIG. 2-9 show different embodiments of a release liner pad according to the invention having one or more score lines;

Figure 10:
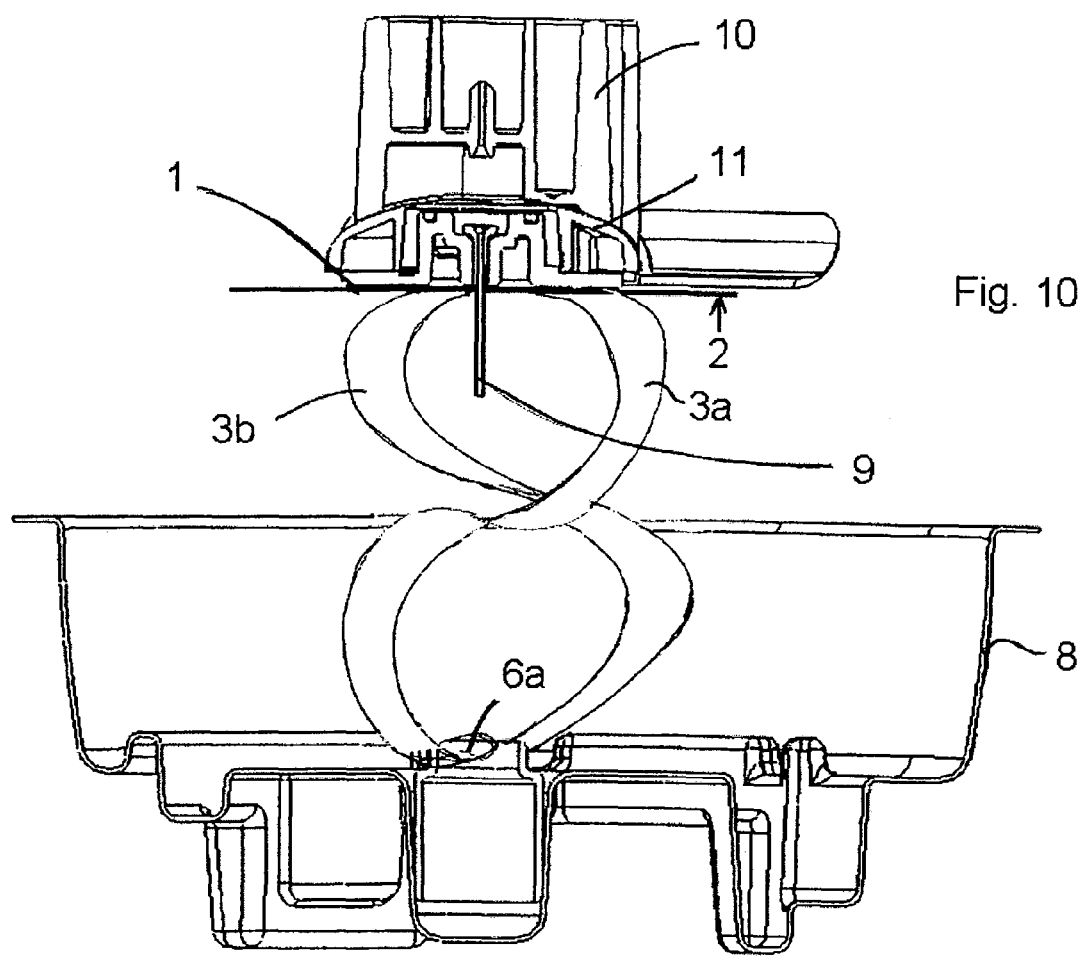
Figure 11C:
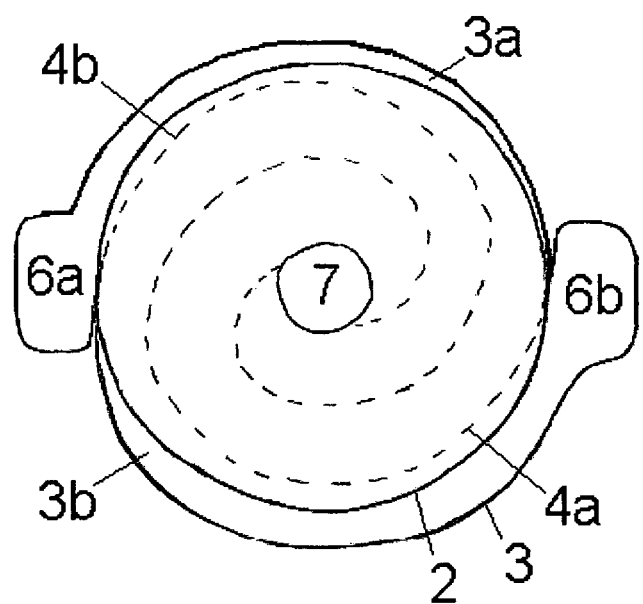

FIG. 10 schematically shows a sectional view of a cannula device according to the invention having a mounting pad with a release liner during removal of the release liner;

FIG. 11a-11c show another embodiment of a release liner in combination with an adhesive layer.

DETAILED DESCRIPTION OF THE PREFERRED EMBODIMENTS

The invention is explained more in detail with reference to the drawings showing preferred embodiments of the invention. These embodiments are not to be construed as limiting the scope of the present invention as set forth in the appended claims.

FIG. 1 shows an embodiment of a mounting pad 1 according to the invention that is suitable for being arranged on the lower face plate of a cannula device or to be used as such as a plaster or a dressing. The mounting pad 1 according to the invention may be configured in various shapes such as substantially circular, oval, triangular, rectangular, etc. The mounting pad comprises in general an adhesive layer 2, which adhesive layer 2 is a skin friendly adhesive known per se, and a removable release liner 3, which covers the adhesive layer 2. The mounting pad 1 in FIG. 1 is shown from above where it is only possible to see the projecting handle parts of the release liner 3 as the adhesive layer 2 covers the central part, both release liner 3 and adhesive layer 2 is provided with a central aperture 7.

FIG. 2-9 show different embodiments of the mounting pad 1 according to the invention where the release liner is provided with score lines 4 of different shape and location. The embodiments in FIG. 2-9 show different embodiments of a release liner being divided into two sections 3a, 3b, each of said sections 3a, 3b is being provided with at least one score line 4 thereby generating a predetermined pattern, which defines each section 3a, 3b of the release liner as a narrow strip.

FIG. 2 shows an embodiment of a release liner 3 used with a mounting pad 1 according to the invention. The release liner 3 is divided into two sections 3a, 3b and the embodiment of FIG. 2a is provided with two projecting parts, a first projecting part 6a and a second projecting part 6b, in the form of tabs. The embodiment of FIG. 2b has no projecting parts, instead of being "projecting parts" the end parts 6a and 6b of the two sections 3a and 3b just end close to the border of the mounting pad but do not extend the edge of the mounting pad or do not extend no more than the surrounding release liner parts. The two projecting tabs 6a, 6b of the release liner 3 protrude from the periphery of the mounting pad 1 and projects beyond the adhesive layer 2. Furthermore, the two projecting tabs 6a, 6b are situated diametrically opposite each other. The release liner 3 is provided with one uninterrupted score line 4, which has its starting point on the periphery of the release liner 3 in the vicinity of the first projecting tab 6a, said score line 4 extending helically and as an unbroken line from this first projecting tab 6a into the centre of the release liner 3 and continuing from the centre of the release liner 3 as a congruent helically line to the vicinity of the second projecting tab 6b at the periphery of the release liner 3 dividing the release liner 3 in sections 3a, 3b. When the two projecting tabs are seized, only little force and short pull-length is required to remove the release liner 3 from the subjacent adhesive layer 2 and the release liner 3 can be peeled in two separate strips simultaneously from the two ends 6a and 6b, leaving the adhesive layer 2 exposed.

Figure 3:
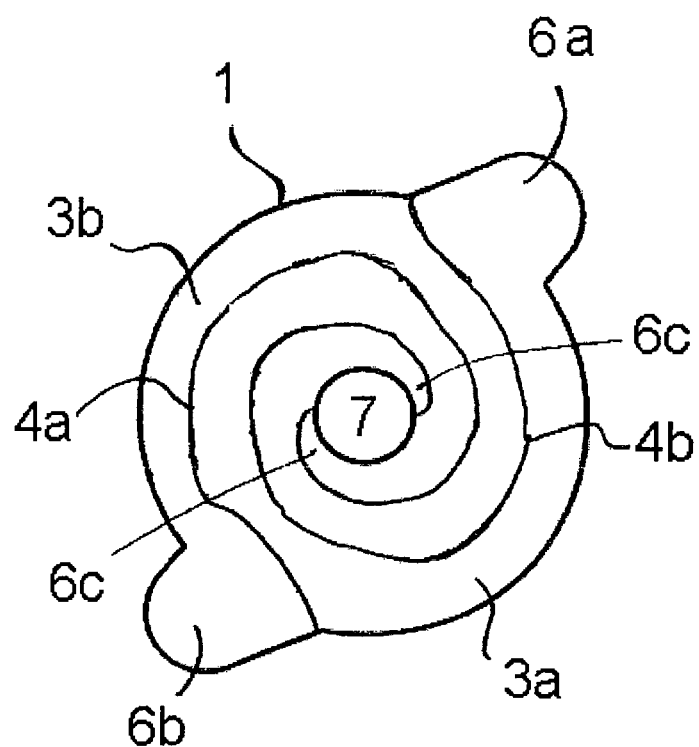
Figure 4:
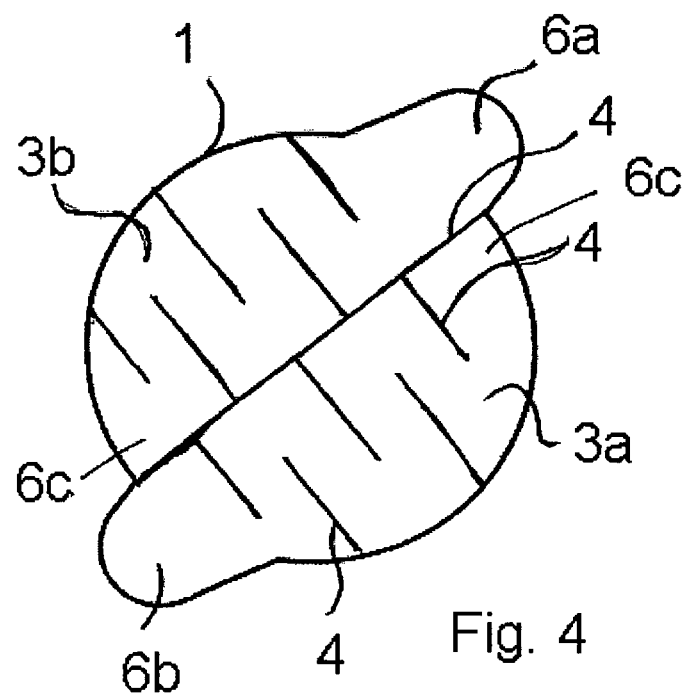
Figure 5:
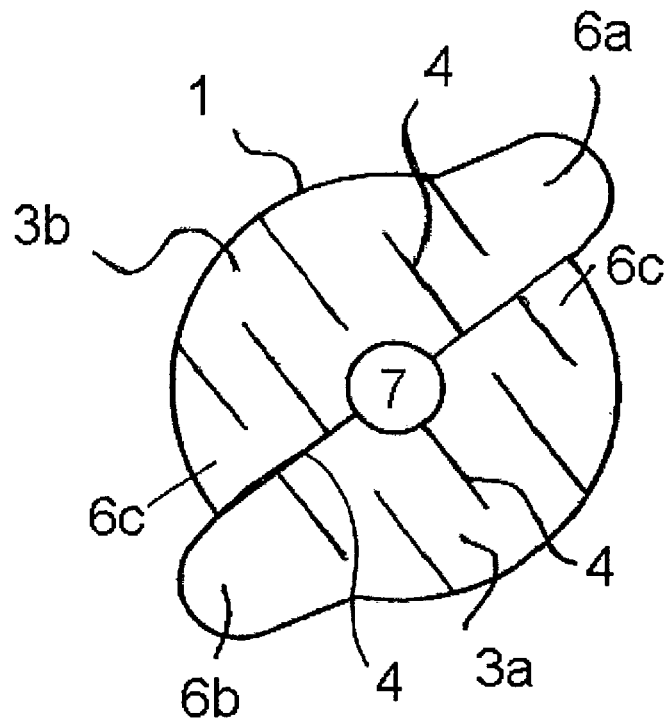
Figure 6:
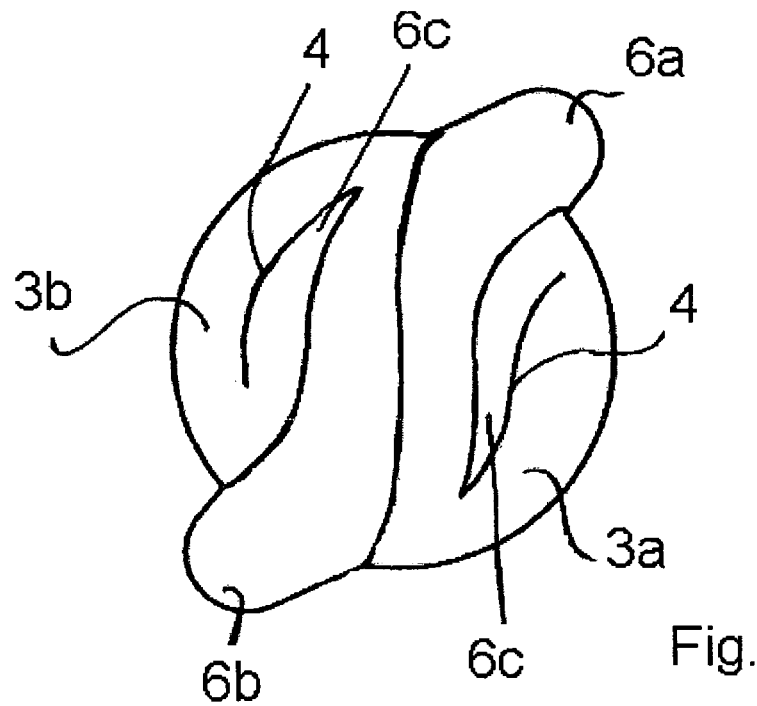
Figure 7:
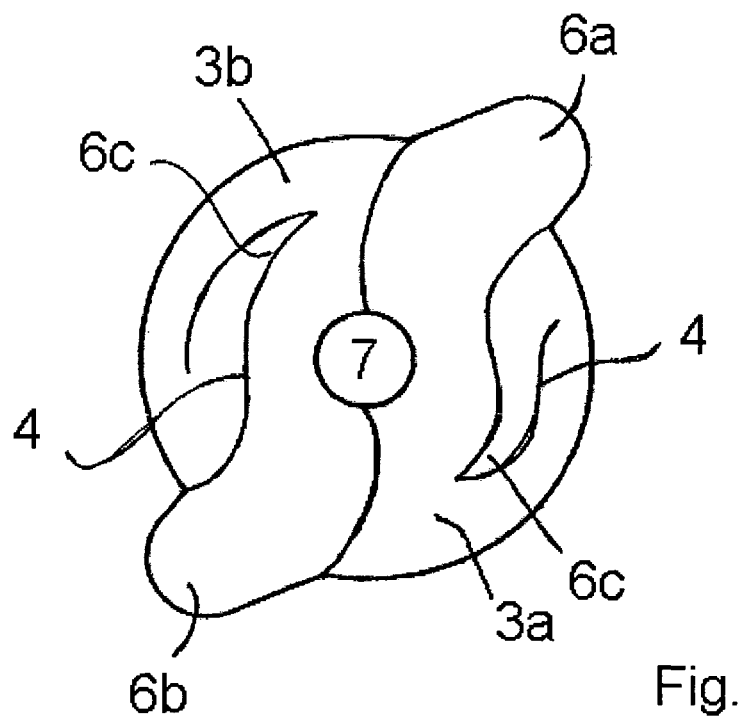
Figure 8:
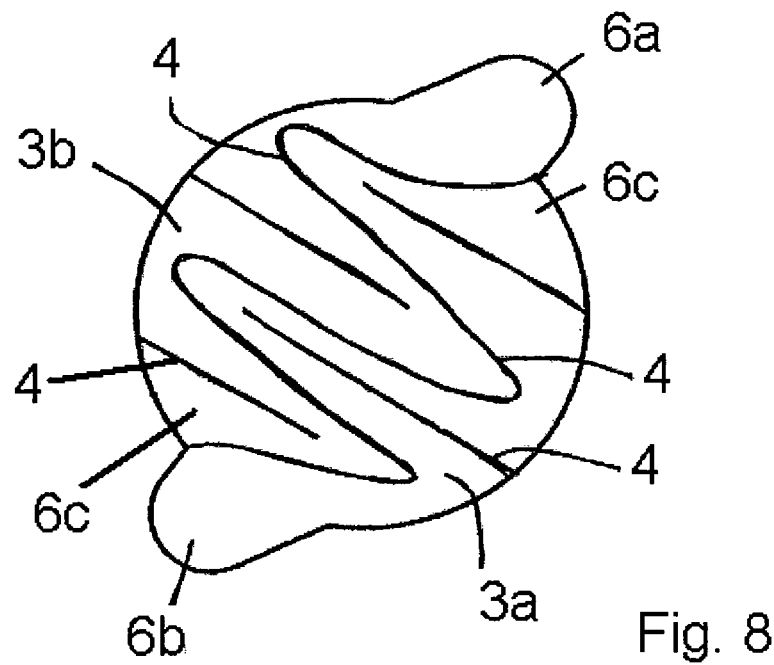
Figure 9:
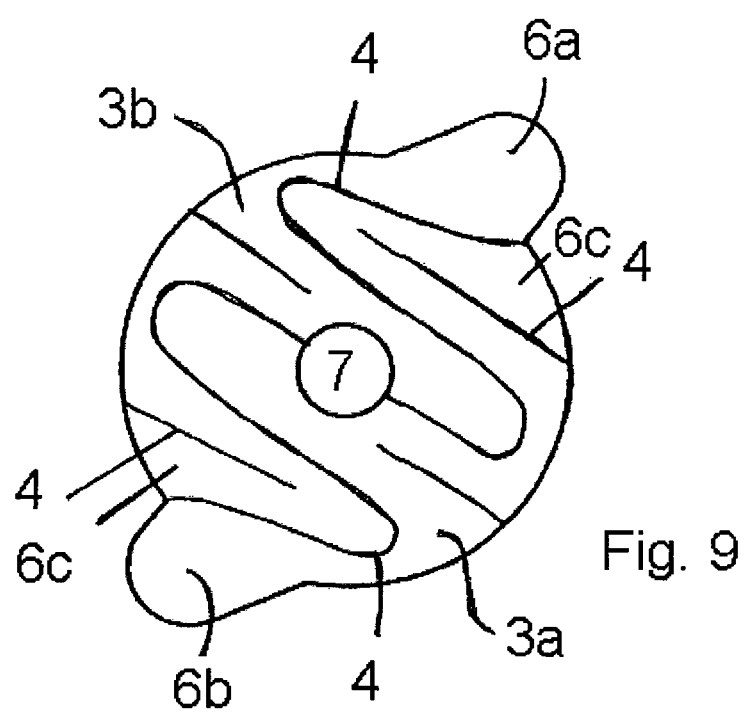

FIG. 3 shows another embodiment of a release liner 3 which also can be used with a mounting pad 1 according to the invention and the release liner 3 is provided with the same features as the embodiment in FIG. 2. Furthermore the release liner is provided with a central aperture 7 and two uninterrupted score lines 4a, 4b extending helically as unbroken lines towards the central aperture 7 of the release liner 3, the first score line 4a having a starting point on the periphery of the release liner in the vicinity of the one projecting tab 6b, and the second score line 4b having a starting point situated diametrically opposite the starting point of the first score line 4a on the periphery of the release liner 3 in the vicinity of the other projecting tab 6a. The two score lines 4a, 4b are arranged in respectively a left-handed and a right-handed spiral and are being parted from each other or situated with a spacing in between defining the wideness of the strips. The score lines 4a, 4b end diametrically opposite each other on the periphery of the central aperture 7. When the tabs are seized, only little force and short pull-length is required to remove the release liner 3 from the subjacent adhesive layer 2 and the release liner 3 can be peeled simultaneously in two individual strips, leaving the adhesive layer 2 exposed.

The release liner 3 covering the adhesive layer 2 of the mounting pad 1 of FIGS. 2-10 is preferably made from siliconized paper or from a sheet of polyethylene which can easily be removed from the adhesive layer 2 without damaging the same.

The score lines 4, 4a, 4b can be in the form of punched or cut dots, slots or interrupted lines which cuts all through the material of the release liner 3, or uninterrupted lines which does not cut all through the material of the release liner but just provide weakened structures. Further, the score lines 4, 4a, 4b defining each section 3a, 3b of the release liner may be formed as a curved score line, such as a helical score line, a sinus curved score line, a straight score line or combinations thereof. The score lines 4, 4a, 4b do not intersect each other. This way, each section 3a, 3b likewise will be shaped according to the score lines 4, 4a and 4b as a narrow strip of curved, helical, sinus or angled shape.

In the embodiments shown in FIGS. 4-9 a first score line 4 proceeds from the first projecting tab 6a to the second projecting tab 6b or from the projecting tabs 6a, 6b to a central aperture 7 and further score lines 4 can extend from the first score line 4 and/or the from the periphery of the release liner 3.

In one embodiment of the invention each strip formed by a section of the release liner 3 has a first end at a projecting tab 6a, 6b and a second end 6c which could be positioned at the periphery or at a central part of the release liner 3 or in between. The first end 6a, 6b can be fixed to a base for fixation of the release liner 3 causing the release liner 3 to be continuously removed when the mounting pad 1 is distanced from the base. This base could e.g. be provided by the packing for the mounting pad 1, or as shown in FIG. 10 for the packing 8 of an infusion set. When a first end of the strips constituting the release liner 3 is fastened to the packing, the first end of strips will be held stationary in relation to the base and automatic release of the release liner will take place when removing the release liner e.g. by pulling a handling part attached to the mounting pad 1, this way the user will completely avoid touching the adhesive layer 2 and handling of the release liner 3 even with reduced dexterity of the hands will become possible.

In use, the release liner is removed from the mounting pad 1 according to the invention by retaining a point of each section 3a, 3b of the release liner at a first end in the vicinity of the projecting tabs 6a, 6b of the mounting pad 1 and afterwards removing the release liner by pulling in a single straight pull.

When pulling the release liner from the adhesive layer in such a single straight upward pull, the release liner is removed in two or more narrow strips. Thereby an even pull with small force needed to remove the release liner is maintained. Further, the pull-length of the release liner is reduced as the release liner is divided into two or more strips, which is removed simultaneously by the single straight upward pull.

In another embodiment the release liner of the mounting pad 1 according to the invention the width of each strip of each section 3a, 3b is less than half the width of the widest point of the mounting pad 1. When the strips are being narrow a reduced force is needed when peeling the release liner from the adhesive layer 2 of the mounting pad 1.

The mounting pad 1 may comprise an aperture 7 and by an aperture is meant a hole or an opening through both the adhesive layer 2 and the release liner 3 of the mounting pad 1. The aperture 7 is located within the periphery of the mounting pad 1 and will normally be located at the central part or near the central part of the mounting pad 1. The aperture 7 can be in any shape or form which allows for e.g. a cannula or a stoma to extend through the aperture 7 such as oval, circular, triangular.

FIG. 10 shows an embodiment of an infusion device according to the invention where a removable release liner 3 covering the adhesive layer 2 of a mounting pad 1 is removed during release of an infusion set 11 from a packaging 8. The infusion set 11 is intended for subcutaneous introduction of a cannula 9 which cannula 9 extends from the proximal side of the infusion set 11. The infusion set 11 is combined with a manual inserter 10 or handling device which inserter 10 makes it possible to handle and insert the infusion device. The mounting pad 1 is placed in connection with a lower face plate of the infusion set 11, and is meant for securing the cannula device which forms part of the infusion set 11 to the skin of the user. The release liner 3 is in this embodiment divided into two sections 3a, 3b by two score lines 4 thereby forming the sections 3a, 3b of the release liner 3 as strips. Each section 3a, 3b forms a narrow helically strip so that the release liner forms a double spiral of the kind shown in FIG. 3. The first end 6a, 6b (only one first end is shown in the figure) of each strip of the release liner 3 closest to the periphery of the mounting pad 1 are connected to an interior surface of the packaging 8 and the rest of the release liner 3 is releasably fastened to the adhesive surface 2. The first end 6a, 6b of the release liner 3 may be fastened to the packaging 8 by gluing, welding or mechanically. When e.g. an inserter (not shown) for automatic insertion of the infusion set is pushed down for connecting to the infusion set 11, the infusion set 11 will be locked to the inserter and at the same time the first end 6a, 6b of each strip of the release liner are pressed down towards the interior surface of the packaging 8 and fastened e.g. with glue, said glue being placed at points corresponding to the first ends 6a, 6b within the interior of the packaging 8. When withdrawing the infusion set 11 from the packaging 8, the release liner 3 is automatically peeled from the adhesive layer 2.

The handling is easy and tearing of the release liner 3 can be avoided. The handling will take place in the same manner as in case the mounting pad 1 is used without an infusion set 11.

In one embodiment the infusion set 11 according to the invention is an infusion set used for infusion of a medicament such as insulin. In another embodiment according to the invention the subcutaneously inserted device is a transcutaneous sensor for measuring the glucose level in a patient.

FIGS. 11a, 11b and 11c show yet another embodiment of a release liner 3 where the start 5 of a score line 4 is completely cut through, actually material has been removed at the start 5 of the score line 4 at the embodiment of FIG. 11a at the periphery of the release liner 3. The start 5 of a score line 4 is defined as a position of a section 3a, 3b of the release liner 3 where the releasing of the section from the adhesive layer 2 initiates. This has the effect that it is easier to initiate the tearing of the score line 4 which then assures an increased success rate for actually removing the release liner 3 from the adhesive layer 2 when pulling the adhesive layer 2 away from the release liner 3. When cutting through the release liner 3 instead of making a score line, the length of the cut through line in the release liner 3 will provide to adjacent edges of release liner 3. The length of the cut through line, i.e. the part where the score line 4 is completely cut through, will normally be less than 2 mm but can have any length.

In the embodiment of FIG. 11a the release liner 3 has an increased surface area compared to the adhesive layer 2, this is shown in FIG. 11a as an increased diameter of the release liner 3 which means that the release liner 3 can be seen from above as a round going strip around the adhesive layer 2 instead of just at the projecting handling parts 6a and 6b. This increased surface of the release liner 3 has the effect that it is possible to provide a start part 5 of a section 3a, 3b close to the periphery of the release liner with little adhesion to the adhesive layer 2 while the section 3a, 3b of the release liner 3 still has a size—especially a certain width—which makes it less likely to be torn when separating the release liner 3 from the adhesive layer 2.

Its therefore possible to at least partly control the adhesion to the adhesive layer by letting a part of each section 3a, 3b extend beyond the adhesive layer 2. One way to do this is to let a defined fraction of the width of the outermost part of each section 3a, 3b extend beyond the adhesive layer 2 i.e. in the longitudinal direction of the strip formed by each section 3a, 3b closest to the outer border of the release liner, the adhesive layer 2 will only cover e.g. half or two-thirds of the release liner section.

In order to make the initiation of the removal of the release liner sections easier, the angle between the two adjacent sections—the angle of the opening provided by the beginning of the score line 4—in the start position should be less than 90°, even less than 30°.

FIG. 11c shows how the score lines 4a and 4b which form the sections 3a and 3b can be positioned below the adhesive layer 2 of the mounting pad.

The features illustrated in FIG. 11a-c can be used in connection with any of the previous described embodiments.

The invention claimed is:

1. A mounting pad comprising an adhesive layer, said adhesive layer further comprising a removable release liner, said release liner being divided into at least two sections, each of the at least two sections of the release liner comprising one or more score lines defining each section of the release liner as a strip, wherein each strip of each section of the release liner has a first end and a second end, each first end is provided with means to fasten the first end to a base of a packaging of the mounting pad for fixation of the release liner thereto.

2. A mounting pad according to claim 1, wherein a start position of a score line defining a first end of a section of the release liner as being different from another part of the release liner is completely cut through forming two adjacent separate edges of the release liner.

3. A mounting pad according to claim 2, wherein the two adjacent edges of the release liner form an angle of less than 30°.

4. A mounting pad according to claim 1, wherein the first end of a section is fastened to an interior surface of the packaging for fixation of the release liner thereto.

5. A mounting pad according to claim 1, wherein a part of each section extends beyond the adhesive layer.

6. A mounting pad according to claim 5, wherein a fraction of the width of an outermost part of each section extends beyond the adhesive layer.

7. A mounting pad according to claim 6, wherein the first end of each section is shaped as a projecting part on a periphery of the release liner.

8. A mounting pad according to claim 7, wherein a projecting part extends beyond the adhesive layer.

9. A mounting pad according to claim 1, wherein the width of each section is less than half the width of the widest point of the mounting pad.

10. A mounting pad according to claim 1, wherein at least a part of the score lines comprises punched or cut dots, slots or interrupted lines.

11. A mounting pad according to claim 1, wherein the at least one score line is helically shaped.

12. A mounting pad according to claim 1, wherein each section of the release liner is helically shaped.

13. A mounting pad according to claim 1, wherein the width of each section increases toward the center of the release liner.

14. A mounting pad according to claim 1, wherein the sections are parted from one another by one uninterrupted score line.

15. A mounting pad according to claim 1, wherein each score line has a starting point near the first end of the release liner.

16. A mounting pad according to claim 1, wherein the adhesive layer is a skin friendly adhesive.

17. A mounting pad according to claim 1, wherein the release liner is made of siliconized paper.

18. A mounting pad according to claim 1, wherein the release liner comprises an aperture.

19. A mounting pad according to claim 18, wherein the aperture is placed at the central part of the mounting pad.

20. A mounting pad according to claim 1, wherein said mounting pad is substantially circular or substantially oval.

21. A cannula device for subcutaneous introduction of a cannula comprising:
    a housing with an upper face plate and a lower face plate and a cannula connected to the lower face plate and
    a mounting pad placed in connection with the lower face plate and for securing the cannula device to the skin; said mounting pad comprising an adhesive layer, said layer further comprising a removable release liner, each of the at least two sections of the release liner comprises one or more score lines forming each section of the release liner as a strip, each strip of each section of the release liner has a first end and a second end, each first end is provided with means to fasten the first end to a base of a packaging of the mounting pad for fixation of the release liner thereto.

22. A cannula device according to claim 21, wherein the first end of each strip is shaped as a projecting part on a periphery of the release liner.

23. A cannula device according to claim 21, wherein the maximum width of each strip is less than half a width of a widest point of the release liner.

24. A cannula device according to claim 21, wherein the release liner comprises an aperture placed in the central part of the mounting pad.

25. A cannula device according to claim 21, wherein said mounting pad is substantially circular or substantially oval.

26. A cannula device according to claim 21, wherein the cannula device is an infusion set.

27. A cannula device according to claim 21, wherein the cannula device is a transcutaneous sensor.

28. A method of removing a release liner from a mounting pad according to claim 1, comprising
   retaining a point of each section of the release liner at the first end of the mounting pad
   removing all sections of the release liner by pulling in a single pull.

* * * * *